United States Patent [19]

Baniel

[11] 4,334,095

[45] Jun. 8, 1982

[54] EXTRACTION OF ORGANIC ACIDS FROM AQUEOUS SOLUTIONS

[75] Inventor: Avraham M. Baniel, Jerusalem, Israel

[73] Assignee: Miles Laboratories, Inc., Elkhart, Ind.

[21] Appl. No.: 194,555

[22] Filed: Oct. 6, 1980

[51] Int. Cl.$^3$ .......................................... C07C 59/265
[52] U.S. Cl. .................................. 562/584; 562/582; 562/589
[58] Field of Search ........................ 562/584, 589, 582

[56] References Cited

U.S. PATENT DOCUMENTS 3,944,606 3/1976 Rieger et al. ........................ 562/584
4,082,788 4/1978 Mims .................................... 562/589

Primary Examiner—Paul J. Killos
Attorney, Agent, or Firm—Louis E. Davidson

[57] ABSTRACT

Organic acids, such as citric acid, malic acid and lactic acid, can be extracted from aqueous solutions thereof by contacting such solutions with a mixture of a water immiscible amine and a water immiscible organic acid dissolved in a suitable water immiscible solvent.

10 Claims, No Drawings

EXTRACTION OF ORGANIC ACIDS FROM AQUEOUS SOLUTIONS

BACKGROUND AND DISCUSSION OF PRIOR ART

Various organic acids, such as citric acid, malic acid, lactic acid and the like, are produced by various techniques and are available in aqueous solutions from which it is desired to recover such acids in a purified and concentrated form.

Citric acid has been commercially removed from aqueous solutions thereof, such as fermentation beer, by the procedure of adding lime to form a precipitate of calcium citrate and then reacting the calcium citrate with aqueous sulfuric acid to form a citric acid solution and insoluble calcium sulfate. This procedure has the disadvantages of requiring expendable lime and sulfuric acid as well as disposal of calcium sulfate.

Liquid-liquid extraction procedures have also been proposed in the prior art. The use of long chain aliphatic amines dissolved in an appropriate solvent to extract organic acids is discussed in J. Soc. Chem. Ind. 67, 48 (1948). U.S. Pat. No. 2,539,472 discloses use of an amine-solvent mixture to extract citric acid, lactic acid, or tartaric acid. The resulting complex requires steam distillation to recover the citric acid, lactic acid or tartaric acid therefrom however. The use of a mixture of amines and hydrocarbons to extract citric acid, lactic acid or oxalic acid is disclosed in British Pat. No. 1,426,018. The recovery of citrate salts using an amine-organic solvent mixture for extraction of citric acid is also disclosed in U.S. Pat. No. 3,944,606. None of the above prior art discloses or suggests the combination of a water immiscible amine and a water immiscible organic acid to extract organic acids, such as citric acid.

SUMMARY OF THE INVENTION

In accordance with the present invention, a process for the extraction of an organic acid from an aqueous solution thereof is provided which comprises contacting such solution with a mixture of a water immiscible amine and a water immiscible organic acid dissolved in a suitable water immiscible solvent. This process is especially useful for the extraction of citric acid.

DESCRIPTION OF THE INVENTION

The aqueous organic acid solutions used as starting material for the process of the present invention are well known. In the case of citric acid, they can be fermentor beers produced by the fermentation of various cultures, such as *Aspergillus niger* on carbohydrates, or they can be citric acid solutions obtained from any other source. The concentration of citric acid is not critical. The present invention has been used to extract citric acid from aqueous solutions thereof containing as low as 1 percent and as high as 20 percent (weight/volume basis) citric acid.

The water immiscible amines useful in the present invention may be primary, secondary, tertiary or quaternary containing at least 12 carbon atoms in aggregate. The preferred amines contain at least 20 carbon atoms in aggregate. These amines may be aliphatic, araliphatic, aromatic, or mixtures or combinations thereof. Examples of useful amines are trilaurylamine, tricaprylylamine, tritridecylamine, trioctylamine, dilaurylamine, dilaurylbenzylamine, a secondary amine having two highly branched aliphatic groups attached to the nitrogen atom and with a molecular weight of about 351 to 393, primary aliphatic amines wherein the aliphatic group is tertiary hydrocarbyl having 18 to 22 carbon atoms, and the like.

The water immiscible organic acids useful in the present invention may be carboxylic acids, alkylphosphoric acids, alkylphosphonic acids, halogen substituted derivatives thereof and mixtures thereof. Such acids should contain at least 12 carbon atoms in aggregate and preferably at least 18 carbon atoms in aggregate. The halogenated derivatives may contain less than 12 carbon atoms so long as the material is water immiscible. Examples of useful acids are oleic acid, diethylhexyl phosphoric acid, 2-bromohexanoic acid, linoleic acid, octanoic acid, 2-bromolauric acid, an aliphatic substituted cyclopentyl carboxylic acid and the like.

The water immiscible solvents useful in the present invention may be aliphatic hydrocarbons, aromatic hydrocarbons, petroleum fractions, hydrocarbons carrying nitro or halo substituents, alcohols, ketones and mixtures thereof. Examples of useful solvents are an aliphatic naphtha (petroleum fraction) having a boiling point range of 179.4°–204.4° C. and an average specific gravity of 0.752 measured at 25° C., xylene, a petroleum fraction having a boiling point range of 140°–210° C., a petroleum fraction having a boiling point range of 180°–210° C., n-octanol, nitrobenzene, a hydrocarbon fraction having a boiling point range of 60°–90° C., n-octane and the like.

The water immiscible amines and water immiscible organic acids are preferably employed in the molar proportion of amine:organic acid from about 0.8:1 to about 1.2:1. Higher proportions of amine are not desirable since the excess of amine will form a complex with citric acid, for example, from which the citric acid could not be conveniently recovered at the same temperature as the extraction. Higher proportions of acid may be necessary in certain combinations of amines and acids in order to obtain the desired eventual recovery of citric acid.

The extraction temperature is not narrowly critical and can be from about 20° C. to about 80° C. The desired acid, such as citric acid, can be conveniently recovered from the amine-acid-solvent phase by back-extraction with water at the same temperature as the initial extraction step.

The combination of amine and acid employed in the process of the present invention to extract water soluble organic acids, such as citric acid, is unexpected when compared to the known prior art. In a conventional extraction process the amine, which is basic, reacts with the citric acid to form a complex salt. This complex salt is then dissociated chemically or at elevated temperature so that the citric acid can be recovered in a back-extracting step. If one initially added an acid to the amine, this acid would be expected to react with the amine and thus reduce the capacity of the amine to react with and extract citric acid. It is thus unobvious and unexpected to employ an amine-acid combination and still have a desirably high extraction capacity. It is further unexpected that this extraction process enables the citric acid to be recovered by back-extraction at the same temperature as the extraction step.

The invention is described in further detail in the following examples:

EXAMPLE 1

A solution of trilaurylamine and oleic acid in a hydrocarbon solvent was prepared by mixing 12.5 g. trilaurylamine and 5.64 g. oleic acid in sufficient amount of a liquid hydrocarbon to produce 100 ml. of solution. The liquid hydrocarbon was an aliphatic naphtha (petroleum fraction) having a boiling point range of 179.4°–204.4° C. and an average specific gravity of 0.752 measured at 25° C. The resulting solution had a molar ratio of trilaurylamine:oleic acid of 1.2:1. Similar solutions were produced having molar ratios of trilaurylamine:oleic acid of 1:1 and 0.8:1. Separate aqueous solutions containing 1 percent, 10 percent and 20 percent, respectively, (weight/volume basis) of citric acid were also prepared.

A 40 ml. portion of each of the above three separate citric acid solutions was placed into three separate 100 ml. containers (a total of nine containers). A 10 ml. portion of each of the above three separate trilaurylamine-oleic acid solutions was placed into three of the above citric acid solution containers so that each of the separate trilaurylamine-oleic acid solutions was contained with each of the separate citric acid solutions. All of the nine containers were then placed in a 20° C. water bath for about 15 min. to equilibrate, were shaken twice, left overnight at 20° C., shaken again and centrifuged for 15 min. at about 2800 RPM. The organic phase of the contents of each of the containers was then analyzed for citric acid. The results are shown below in Table 1.

TABLE 1

| Mole Ratio Trilauryl- amine: Oleic Acid | Organic Phase Citric Acid Concentration (Moles/Liter) Initial Citric Acid Concentration in Aqueous Phase (weight/volume basis) | | |
|---|---|---|---|
| | 1% | 10% | 20% |
| 1.2:1 | 0.012 | 0.084 | 0.130 |
| 1:1 | 0.013 | 0.069 | 0.105 |
| 0.8:1 | 0.013 | 0.029 | 0.069 |

It can be seen from the above data that a mixture of trilaurylamine and oleic acid in various concentrations in a hydrocarbon solvent can extract citric acid from aqueous solutions having various concentrations thereof.

EXAMPLE 2

A solution of trilaurylamine and diethylhexyl phosphoric acid in a hydrocarbon solvent was prepared by mixing 12.5 g. trilaurylamine and 6.44 g. diethylhexyl phosphoric acid in sufficient amount of the liquid hydrocarbon described in Example 1 to produce 100 ml. of solution having a molar ratio of trilaurylamine:diethylhexyl phosphoric acid of 1.2:1. Similar solutions were produced having molar ratios of trilaurylamine:diethylhexyl phosphoric acid of 1:1 and 0.8:1.

A 40 ml. portion of each of the three separate citric acid solutions described in Example 1 was placed into three separate 100 ml. containers (a total of nine containers). A 5 ml portion of each of the above three separate trilaurylamine-diethylhexyl phosphoric acid solutions was placed into each of the three containers containing the 1 percent citric acid solutions. A 10 ml. portion of each of the above three separate amine-acid solutions was placed into six of the above containers containing respectively, the 10 and 20 percent citric acid solutions. All of the nine containers were then shaken and placed in a 20° C. water bath for about 15 min. They were then centrifuged for about 15 min. at about 2800 RPM. The organic phase of the contents of each of the containers was analyzed for citric acid. The results are shown below in Table 2.

TABLE 2

| Mole Ratio Trilaurylamine: Diethylhexyl Phosphoric Acid | Organic Phase Citric Acid Concentration (Moles/Liter) Initial Citric Acid Concentration in Aqueous Phase (weight/volume basis) | | |
|---|---|---|---|
| | 1% | 10% | 20% |
| 1.2:1 | 0.045 | 0.081 | 0.119 |
| 1:1 | 0.031 | 0.055 | 0.070 |
| 0.8:1 | 0.035 | 0.050 | 0.058 |

It can be seen from the above data that a mixture of trilaurylamine and diethylhexyl phosphoric acid in various concentrations in a hydrocarbon solvent can extract citric acid from aqueous solutions having various concentrations thereof.

EXAMPLE 3

A solution of trilaurylamine and 2-bromohexanoic acid in a hydrocarbon solvent was prepared by mixing appropriate quantities of trilaurylamine and 2-bromohexanoic acid in sufficient amount of the liquid hydrocarbon described in Example 1 to produce 100 ml. of solution having a molar ratio of trilaurylamine:2-bromohexanoic acid of 1.2:1. Similar solutions were produced having molar ratios of trilaurylamine:2-bromohexanoic acid of 1:1 and 0.8:1.

A 25 ml. portion of each of the three separate citric acid solutions described in Example 1 was placed into three separate 100 ml. containers (a total of nine containers). A 5 ml. portion of each of the above three separate amine-acid solutions was placed into three of the above citric acid solutions containers so that each of the separate amine-acid solutions was contacted with each of the separate citric acid solutions. All of the nine containers were then placed in a 20° C. water bath for about 15 min., shaken and then replaced into the water bath for about 15 min., shaken again and centrifuged for about 15 min. at 2800 RPM. The organic phase of the contents of each of the containers was analyzed for citric acid. The results are shown below in Table 3.

TABLE 3

| Mole Ratio Trilaurylamine: 2-Bromohexanoic Acid | Organic Phase Citric Acid Concentration (Moles/Liter) Initial Citric Acid Concentration in Aqueous Phase (weight/volume basis) | | |
|---|---|---|---|
| | 1% | 10% | 20% |
| 1.2:1 | 0.012 | 0.052 | 0.075 |
| 1:1 | 0.005 | 0.030 | 0.043 |
| 0.8:1 | 0.004 | 0.008 | 0.011 |

It can be seen from the above data that a mixture of trilaurylamine and 2-bromohexanoic acid in various concentrations in a hydrocarbon solvent can extract citric acid from various aqueous solutions having various concentrations thereof.

EXAMPLE 4

A 200 ml. quantity of a solution of trilaurylamine and oleic acid in a hydrocarbon solvent having a molar ratio of trilaurylamine:oleic acid of 1.2:1 was prepared as described in Example 1. A 50 ml. portion of this solution was placed into each of four centrifuge tubes. Into each centrifuge tube was also placed a 75 ml. portion of an aqueous fermentor beer containing 17 percent citric acid (weight/volume basis). The fermentor beer also contained 1889 ppm sulfate ions. All the centrifuge tubes were placed in a 40° C. water bath for 15 min., were shaken for 5 min. on a shaker and then centrifuged for 20 min. at 2800 RPM. The organic phases of all the tubes were than removed and pooled. Analysis of the organic phase indicated that it contained 5.6 percent citric acid (weight/volume basis).

The 200 ml. of organic phase was divided into two 100 ml. portions. One portion was mixed with 20 ml. water at 40° C. for 15 min., shaken and then centrifuged for 20 min. at 2800 RPM. The aqueous and organic phases were separated and the aqueous phase was then contacted with the other 100 ml. portion of the initial organic phase and treated as described above. The aqueous and organic phases were then separated and the aqueous phase was analyzed to contain 8.12 percent (weight/volume basis) citric acid and 24 ppm sulfate ions.

This example shows that the process of the present invention can conveniently extract citric acid from impure solutions thereof and that the extracted acid can be easily recovered in a purified state by back-extraction with water at the same temperature as the initial extraction.

Carbonizables in citric acid solutions are measured by contacting 10 ml. concentrated sulfuric acid at 0° C. with 1 ml. of sample (prediluted to obtain a final O.D. in the range of 0.1-0.3) in a test tube in an ice bath. The mixture is shaken, then heated for 1 hour at 90° C. It is cooled to room temperature and the O.D. measured at 497 nm. The above citric acid-containing fermentor beer had a carbonizable content represented by an O.D. of 24.4. The back-extract aqueous citric acid had an O.D. of 0.33. This also shows that the process of the present invention also purifies citric acid solutions by removing undesirable carbonizables.

The process of the present invention is compared to the prior art in the following example.

EXAMPLE 5

A solution of trilaurylamine and oleic acid in a hydrocarbon solvent having a molar ratio of trilaurylamine:oleic acid of 1.2:1 was prepared as described in Example 1. A comparison solution representing the prior art was prepared by mixing trilaurylamine, octanol and the liquid hydrocarbon used in Example 1 in the ratios of 36 g. trilaurylamine, 5 g. octanol and 57 g. liquid hydrocarbon. Separate 55 ml. portions of aqueous citric acid solutions containing either 1 percent or 20 percent (weight/volume basis) citric acid were separately contacted with 10 ml. portions of the above trilaurylamine-oleic acid or trilaurylamine-octanol solutions at either 20° C. or 70° C. After temperature equilibration for about 15 min., they were shaken three times and centrifuged for 5 min. at 10,000 RPM. There was clean phase separation with no emulsion formation. The organic phase of each sample was analyzed for citric acid content. The results are shown in Table 4 below:

TABLE 4

| Solvent System | Temp. 0° C. | Organic Phase Citric Acid Concentration (Moles/Liter) Initial Citric Acid Concentration in Aqueous Phase (Weight/Volume Basis) | |
|---|---|---|---|
| | | 1% | 20% |
| Trilaurylamine Oleic | 20 | 0.106 | 0.298 |
| Trilaurylamine Oleic | 70 | 0.030 | 0.267 |
| Trilaurylamine Octanol | 20 | 0.110 | 0.427 |
| Trilaurylamine Octanol | 70 | 0.018 | 0.364 |

It can be seen from the above data that the process of the present invention is less temperature sensitive than is a related prior art process. The amount of citric acid extracted by the prior art process from a 1 percent citric acid solution was reduced by 84 percent when the extraction temperature was increased from 20° C. to 70° C. In contrast to this, the amount of citric acid extracted by the process of the present invention was reduced by only 72 percent under the same conditions. The amount of citric acid extracted by the prior art process from a 20 percent citric acid solution was reduced by 15 percent when the extraction temperature was increased from 20° C. to 70° C. In contrast to this, the amount of citric acid extracted by the process of the present invention was reduced by only 10 percent under the same conditions.

EXAMPLE 6

A solution in a hydrocarbon solvent of oleic acid and a primary aliphatic amine consisting of a mixture of primary amines wherein the aliphatic group is tertiary hydrocarbyl having 18 to 22 carbon atoms (Primene JM-T) was prepared by mixing sufficient amounts of the amine and acid in the liquid hydrocarbon described in Example 1 to produce a concentration of 0.5 M amine and 0.5 M acid (molar ratio of amine:acid of 1:1). An aqueous solution of citric acid containing 20 percent citric acid (weight/volume basis) was mixed with the above amine-acid-hydrocarbon mixture in a volume ratio of 8:30 (organic phase:aqueous phase) in a 50 ml. centrifuge tube. The mixture was placed in a 40° C. water bath for about 30 min. It was then shaken four times. Each shaking period was about 1 min. with a separation of about 15 min. between periods. When the mixture was not being shaken, it remained in the water bath. It then stood overnight in the water bath. The organic phase was analyzed to contain 0.303 moles/liter citric acid. This procedure was repeated with fresh solutions at 80° C., and the organic phase contained 0.304 moles/liter citric acid.

EXAMPLE 7

A solution in a hydrocarbon solvent of linoleic acid and a secondary amine having two highly branched aliphatic groups attached to the nitrogen atom and with a molecular weight of about 351 to 393 (Amberlite LA-1) was prepared by mixing sufficient amounts of the amine and acid in the liquid hydrocarbon described in Example 1 to produce a concentration of 0.4 M amine and 0.5 M acid (molar ratio of amine:acid of 0.8:1). An aqueous solution of citric acid having the same concentration as Example 6 was mixed with the amine-acid hydrocarbon mixture in the same way as described in Example 6. The organic phase from the 40° C. extraction contained 0.174 moles/liter citric acid and the organic phase from the 80° C. extraction contained 0.195 moles/liter citric acid.

EXAMPLE 8

A solution of trilaurylamine and octanoic acid in a hydrocarbon solvent was prepared by mixing sufficient amounts of the amine and acid in the liquid hydrocarbon described in Example 1 to produce a concentration of 0.5 M amine and 0.5 M acid (molar ratio of amine:acid of 1:1). An aqueous solution of citric acid having the same concentration as in Example 6 was mixed with the amine-acid-hydrocarbon mixture in the same way as described in Example 6. The organic phase from the 40° C. extraction contained 0.269 moles/liter citric acid, and the organic phase from the 80° C. extraction contained 0.197 moles/liter citric acid.

EXAMPLE 9

A solution is a hydrocarbon solvent of trilaurylamine and an aliphatic substituted cyclopentyl carboxylic acid comprising a mixture of compounds having the general formula:

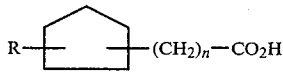

wherein R is one or more aliphatic groups and "n" is an integer from 0 to 4 and having an average molecular weight of 200 to 300 was prepared by mixing sufficient amounts of the amine and acid in the liquid hydrocarbon described in Example 1 to produce a concentration of 0.5 M amine and 0.5 M acid (molar ratio of amine:acid of 1:1). An aqueous solution of citric acid having the same concentration as in Example 6 was mixed with the amine-acid-hydrocarbon mixture in the same way as described in Example 6. The organic phase from the 40° C. extraction contained 0.246 moles/liter citric acid and the organic phase from the 80° C. extraction contained 0.177 moles/liter citric acid.

EXAMPLE 10

A solution of trilaurylamine and 2-bromolauric acid in a hydrocarbon solvent was prepared by mixing sufficient amounts of the amine and acid in the liquid hydrocarbon described in Example 1 to produce a concentration of 0.5 M amine and 0.5 M acid (molar ratio of amine:acid of 1:1). An aqueous solution of citric acid having the same concentration as in Example 6 was mixed with the amine-acid-hydrocarbon mixture in the same way as described in Example 6. The organic phase from the 40° C. extraction contained 0.145 moles/liter citric acid, and the organic phase from the 80° C. extraction contained 0.145 moles/liter citric acid.

It is noted that the results in Examples 6–10 above show that there is substantially no temperature effect on the extraction process of the present invention when extractions at 40° C. and 80° C. are compared.

EXAMPLE 11

A 200 ml. solution of 0.6 M trilaurylamine and 0.5 M oleic acid in the liquid hydrocarbon described in Example 1 was prepared having a concentration of 0.6 M amine and 0.5 M acid (amine:acid molar ratio of 1.2:1). This solution was then mixed with 300 ml. of an aqueous solution of 20 percent citric acid (weight/volume basis). The resulting mixture was shaken, placed in a 40° C. water bath for about 15 min., centrifuged for about 15 min. at 2800 RPM, and the organic and aqueous phases were separated and analyzed to contain respectively, 0.278 moles/liter citric acid and 16.1 percent citric acid (weight/volume basis). This organic phase was then split into two separate 85 ml. portions. The first portion was mixed with 20 ml. water, shaken, placed in a 40° C. water bath for about 15 min., centrifuged for about 15 min. at 2800 RPM, and the organic and aqueous phases were separated and analyzed to contain respectively, 0.227 moles/liter citric acid and 6.4 percent citric acid. This organic phase was then mixed with 40 ml. of an aqueous solution containing 20 percent trisodium citrate, shaken, placed in a 40° C. water bath for about 15 min., centrifuged for about 15 min. at 2800 RPM, and the organic phase was separated and analyzed to contain 0.06 moles/liter citric acid. The second portion of the above split organic phase was mixed with the 20 ml. of water which had previously been mixed with the first portion of the split organic phase, shaken, placed in a 40° C. water bath for about 15 min., centrifuged for about 15 min. at 2800 RPM, and the organic and aqueous phases were separated. The aqueous phase was analyzed to contain 9.5 percent (weight/volume basis) citric acid. The organic phase was analyzed to contain 0.257 moles/liter citric acid.

It can be seen from the above data that citric acid can be easily extracted from an aqueous solution thereof by a mixture of trilaurylamine and oleic acid in a hydrocarbon solvent and that the extracted citric acid can be easily recovered by back-extraction with water at the same temperature as the extraction. Residual citric acid in the organic phase can be removed by back-extraction with trisodium citrate. This also exemplifies back-extraction with an alkali salt to recover the extracted acid as an alkali salt.

EXAMPLE 12

A 200 ml. solution of trilaurylamine, oleic acid and the liquid hydrocarbon described in Example 1 was prepared as described in Example 11. This solution was then mixed with 300 ml. of an aqueous solution of 20 percent malic acid (weight/volume basis). The resulting mixture was shaken, placed in a 40° C. water bath for about 15 min., centrifuged for about 15 min. at 2800 RPM, and the organic and aqueous phases were separated and analyzed. The aqueous phase contained 17.0 percent malic acid (weight/volume basis). The organic phase, which contained 0.400 M malic acid, was then split into two separate 85 ml. portions. The first portion was mixed with 20 ml. water, shaken, placed in a 40° C. water bath for about 15 min., centrifuged for about 15 min. at 2800 RPM, and the organic phase was separated and analyzed to contain 0.237 M malic acid. The second portion of the above split organic phase was then mixed with the 20 ml. of water which had previously been in contact with the first portion of the split organic phase. These materials were shaken, placed in a 40° C. water bath for about 15 min., centrifuged for about 15 min. at 2800 RPM, and the organic and aqueous phases were separated and analyzed. The organic phase contained 0.303 M malic acid, and the aqueous phase contained 12.8 percent (weight/volume basis) malic acid.

The above example shows that malic acid can be extracted by the amine-acid-hydrocarbon process of the present invention and can be easily recovered by back-extraction with water at the same temperature as the extraction.

EXAMPLE 13

A 200 ml. solution of trilaurylamine, oleic acid and the liquid hydrocarbon described in Example 1 was prepared as described in Example 11. This solution was then mixed with 300 ml. of an aqueous solution of 20 percent lactic acid (weight/volume basis). The resulting mixture was shaken, placed in a 40° C. water bath for about 15 min., centrifuged for about 15 min. at 2800 RPM, and the organic and aqueous phases were separated and analyzed. The aqueous phase contained 16.0 percent lactic acid (weight/volume basis). The organic phase, which contained 0.696 M lactic acid, was then split into two separate 85 ml. portions. The first portion was mixed with 20 ml. water, shaken, placed in a 40° C. water bath for about 15 min., centrifuged for about 15 min. at 2800 RPM, and the organic phase was separated and analyzed to contain 0.471 M lactic acid. The second portion of the above split organic phase was then mixed with the 20 ml. of water which had previously been in contact with the first portion of the split organic phase. These materials were shaken, placed in a 40° C. water bath for about 15 min., centrifuged for about 15 min. at 2800 RPM, and the organic and aqueous phases were separated and analyzed. The organic phase contained 0.548 M lactic acid, and the aqueous phase contained 14.8 percent (weight/volume basis) lactic acid.

The above example shows that lactic acid can be extracted by the amine-acid-hydrocarbon process of the present invention and can be easily recovered by back-extraction with water at the same temperature as the extraction.

The following example describes the use of the extraction process of the present invention to extract hydrochloric acid.

EXAMPLE 14

A 200 ml. solution of trilaurylamine, oleic acid and the liquid hydrocarbon described in Example 1 was prepared as described in Example 11. This solution was then mixed with 300 ml. of a 1 N aqueous solution of hydrochloric acid. The resulting mixture was shaken, placed in a 40° C. water bath for about 15 min., centrifuged for about 15 min. at 2800 RPM, and the organic and aqueous phases were separated and analyzed. The aqueous phase contained 0.682 M hydrochloric acid. The organic phase which contained 0.539 M hydrochloric acid, was then split into two separate 85 ml. portions. The first portion was mixed with 20 ml. water, shaken, placed in a 40° C. water bath for about 15 min., centrifuged for about 15 min. at 2800 RPM, and the organic phase was separated and analyzed to contain 0.520 M hydrochloric acid. The second portion of the above split organic phase was then mixed with the 20 ml. of water which had previously been in contact with the first portion of the split organic phase. These materials were shaken, placed in a 40° C. water bath for about 15 min., centrifuged for about 15 min. at 2800 RPM, and the organic and aqueous phases were separated and analyzed. The organic phase contained 0.513 M hydrochloric acid and the aqueous phase contained 0.121 M hydrochloric acid.

It can be seen from the above example that the amine in the process of the present invention reacts with the strong mineral hydrochloric acid. This resulting complex is not easily broken down by water in a back-extraction to enable the hydrochloric acid to be recovered in an aqueous solution.

What is claimed is:

1. A process for the extraction of an organic acid selected from the class consisting of citric acid, malic acid and lactic acid from an aqueous solution thereof which comprises contacting such solution with a mixture of a water immiscible amine and a water immiscible organic acid dissolved in a suitable water immiscible solvent.

2. A process according to claim 1 wherein the water immiscible amine contains at least 12 carbon atoms in aggregate.

3. A process according to claim 1 wherein the water immiscible amine contains at least 20 carbon atoms in aggregate.

4. A process according to claim 1 wherein the water immiscible amine is trilaurylamine.

5. A process according to claim 1 wherein the water immiscible organic acid is selected from the class consisting of carboxylic acids, alkylphosphoric acids, alkylphosphonic acids, and halogen substituted derivatives thereof.

6. A process according to claim 1 wherein the water immiscible organic acid is selected from the class consisting of oleic acid, diethylhexyl phosphoric acid, 2-bromohexanoic acid, linoleic acid, octanoic acid, 2-bromolauric acid and an aliphatic substituted cyclopentyl carboxylic acid.

7. A process according to claim 1 wherein the molar proportion of amine:organic acid is from about 0.8:1 to about 1.2:1.

8. A process according to claim 1 wherein the suitable water immiscible solvent is selected from the class consisting of aliphatic hydrocarbons, aromatic hydrocarbons, petroleum fractions, hydrocarbons carrying nitro or halo substituents, alcohols, ketones and mixtures thereof.

9. A process according to claim 1 carried out at a temperature from about 20° C. to about 80° C.

10. A process according to claim 1 wherein the water immiscible solvent mixture is then contacted with water to back-extract and recover the extracted organic acid at the same temperature as the initial extraction.

* * * * *